(12) United States Patent
Panesar et al.

(10) Patent No.: US 9,310,322 B2
(45) Date of Patent: Apr. 12, 2016

(54) X-RAY SECURITY INSPECTION MACHINE

(75) Inventors: Baljinder Singh Panesar, Hayes (GB); Douglas R. Gillard-Hickman, Crowborough (GB)

(73) Assignee: Rapiscan Systems, Inc., Torrance, CA (US)

( * ) Notice: Subject to any disclaimer, the term of this patent is extended or adjusted under 35 U.S.C. 154(b) by 796 days.

(21) Appl. No.: 13/489,377

(22) Filed: Jun. 5, 2012

(65) Prior Publication Data

US 2013/0001048 A1    Jan. 3, 2013

Related U.S. Application Data

(63) Continuation of application No. 12/715,463, filed on Mar. 2, 2010, now Pat. No. 8,213,570, which is a continuation of application No. 11/817,119, filed as application No. PCT/GB2006/000690 on Feb. 27, 2006, now Pat. No. 7,702,069.

(51) Int. Cl.
*G01N 23/04* (2006.01)

(52) U.S. Cl.
CPC ..................... *G01N 23/04* (2013.01)

(58) Field of Classification Search
CPC ............... G01N 23/04; G01N 23/046; G01N 2223/642; G01N 2223/645; G01N 2223/646; G01N 2223/66; G01N 2223/639; B65G 15/12; B65G 15/14; B65G 15/56; B65G 15/60; B65G 15/62; B65G 15/64; B65G 15/58
USPC ............... 378/19, 57; 198/606, 837, 840, 841
See application file for complete search history.

(56) References Cited

U.S. PATENT DOCUMENTS

| | | | |
|---|---|---|---|
| 2,031,400 A * | 2/1936 | Wilcox | ..................... 425/395 |
| 2,831,123 A | 4/1958 | Daly | |
| 3,766,387 A | 10/1973 | Heffan et al. | |
| 3,784,837 A | 1/1974 | Holmstrom | |
| RE28,544 E | 9/1975 | Stein et al. | |
| 4,047,035 A | 9/1977 | Dennhoven et al. | |
| 4,139,771 A | 2/1979 | Dennhoven et al. | |
| 4,210,811 A | 7/1980 | Dennhoven et al. | |
| 4,216,499 A | 8/1980 | Kunze et al. | |

(Continued)

FOREIGN PATENT DOCUMENTS

JP        2002082070        3/2002

OTHER PUBLICATIONS

International Search Report, May 31, 2006.

(Continued)

*Primary Examiner* — Toan Ton
*Assistant Examiner* — Mona M Sanei
(74) *Attorney, Agent, or Firm* — Novel IP

(57) ABSTRACT

The present specification discloses an X-ray security inspection machine that has a machine housing defining an X-ray tunnel for receiving an article to be inspected, a conveyor belt for conveying the article, two rollers for receiving and moving the conveyor belt, and a conveyor belt tracking device positioned along the path between the two rollers. The conveyor belt tracking device has a mounting bracket for mounting the conveyor belt tracking device to the inspection machine and a guide frame with an upper portion and a lower portion, where the upper portion and lower portion are spaced apart from each other and the conveyor belt passes through the space between the upper portion and lower portion.

7 Claims, 6 Drawing Sheets

(56) References Cited

U.S. PATENT DOCUMENTS

| | | |
|---|---|---|
| 4,239,969 A | 12/1980 | Galetta et al. |
| 4,366,382 A | 12/1982 | Kotowski |
| 4,430,568 A | 2/1984 | Yoshida et al. |
| 4,566,113 A | 1/1986 | Donges et al. |
| 4,599,740 A | 7/1986 | Cable |
| 4,641,330 A | 2/1987 | Herwig et al. |
| 4,736,401 A | 4/1988 | Donges et al. |
| 4,788,704 A | 11/1988 | Donges et al. |
| 4,825,454 A | 4/1989 | Annis et al. |
| 4,884,289 A | 11/1989 | Glockmann et al. |
| 4,979,202 A | 12/1990 | Siczek et al. |
| 4,991,189 A | 2/1991 | Boomgaarden et al. |
| 5,022,062 A | 6/1991 | Annis |
| 5,041,728 A | 8/1991 | Spacher et al. |
| 5,065,418 A | 11/1991 | Bermbach et al. |
| 5,091,924 A | 2/1992 | Bermbach et al. |
| 5,098,640 A | 3/1992 | Gozani et al. |
| 5,179,581 A | 1/1993 | Annis |
| 5,181,234 A | 1/1993 | Smith |
| 5,182,764 A | 1/1993 | Peschmann et al. |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis et al. |
| 5,313,511 A | 5/1994 | Annis et al. |
| 5,367,552 A | 11/1994 | Peschmann |
| 5,379,334 A | 1/1995 | Zimmer et al. |
| 5,493,596 A | 2/1996 | Annis |
| 5,503,424 A | 4/1996 | Agopian |
| 5,600,303 A | 2/1997 | Husseiny et al. |
| 5,638,420 A | 6/1997 | Armistead |
| 5,642,393 A | 6/1997 | Krug et al. |
| 5,642,394 A | 6/1997 | Rothschild |
| 5,666,393 A | 9/1997 | Annis |
| 5,687,210 A | 11/1997 | Maitrejean et al. |
| 5,692,028 A | 11/1997 | Geus et al. |
| 5,751,837 A | 5/1998 | Watanabe et al. |
| 5,764,683 A | 6/1998 | Swift et al. |
| 5,768,334 A | 6/1998 | Maitrejean et al. |
| 5,787,145 A | 7/1998 | Geus |
| 5,805,660 A | 9/1998 | Perion et al. |
| 5,835,558 A | 11/1998 | Maschke et al. |
| 5,838,759 A | 11/1998 | Armistead |
| 5,903,623 A | 5/1999 | Swift et al. |
| 5,910,973 A | 6/1999 | Grodzins |
| 5,930,326 A | 7/1999 | Rothschild et al. |
| 5,940,468 A | 8/1999 | Huang et al. |
| 5,970,113 A | 10/1999 | Ruth |
| 5,974,111 A | 10/1999 | Krug et al. |
| 6,031,890 A | 2/2000 | Bermbach et al. |
| 6,058,158 A | 5/2000 | Eiler |
| 6,058,159 A * | 5/2000 | Conway et al. ............... 378/68 |
| 6,067,344 A | 5/2000 | Grodzins et al. |
| 6,081,580 A | 6/2000 | Grodzins et al. |
| 6,094,472 A | 7/2000 | Smith |
| 6,151,381 A | 11/2000 | Grodzins et al. |
| 6,188,747 B1 | 2/2001 | Geus et al. |
| 6,192,101 B1 | 2/2001 | Grodzins |
| 6,192,104 B1 | 2/2001 | Adams |
| 6,195,413 B1 | 2/2001 | Geus et al. |
| 6,198,795 B1 | 3/2001 | Naumann et al. |
| 6,218,943 B1 | 4/2001 | Ellenbogen |
| 6,249,567 B1 | 6/2001 | Rothschild et al. |
| 6,252,929 B1 | 6/2001 | Swift et al. |
| 6,256,369 B1 | 7/2001 | Lai |
| 6,278,115 B1 | 8/2001 | Annis et al. |
| 6,282,260 B1 | 8/2001 | Grodzins |
| 6,292,533 B1 | 9/2001 | Swift et al. |
| 6,301,326 B2 | 10/2001 | Bjorkholm |
| 6,301,327 B1 | 10/2001 | Martens et al. |
| 6,304,627 B1 | 10/2001 | Horbaschek |
| 6,304,629 B1 | 10/2001 | Conway et al. |
| 6,320,933 B1 | 11/2001 | Grodzins et al. |
| 6,356,620 B1 | 3/2002 | Rothschild et al. |
| 6,424,695 B1 | 7/2002 | Grodzins et al. |
| 6,434,219 B1 | 8/2002 | Rothschild et al. |
| 6,435,715 B1 | 8/2002 | Betz et al. |
| 6,442,233 B1 | 8/2002 | Grodzins et al. |
| 6,445,765 B1 | 9/2002 | Frank et al. |
| 6,453,003 B1 | 9/2002 | Springer et al. |
| 6,453,007 B2 | 9/2002 | Adams et al. |
| 6,456,684 B1 | 9/2002 | Mun et al. |
| 6,459,755 B1 | 10/2002 | Li |
| 6,459,761 B1 | 10/2002 | Grodzins et al. |
| 6,459,764 B1 | 10/2002 | Chalmers |
| 6,473,487 B1 | 10/2002 | Le |
| RE37,899 E | 11/2002 | Grodzins et al. |
| 6,483,894 B2 | 11/2002 | Hartick et al. |
| 6,507,025 B1 | 1/2003 | Verbinski et al. |
| 6,532,276 B1 | 3/2003 | Hartick et al. |
| 6,542,574 B2 | 4/2003 | Grodzins |
| 6,542,578 B2 | 4/2003 | Ries et al. |
| 6,542,580 B1 | 4/2003 | Carver et al. |
| 6,546,072 B1 | 4/2003 | Chalmers |
| 6,552,346 B2 | 4/2003 | Verbinski et al. |
| 6,563,903 B2 | 5/2003 | Kang et al. |
| 6,580,778 B2 | 6/2003 | Meder |
| 6,584,170 B2 | 6/2003 | Aust et al. |
| 6,597,760 B2 | 7/2003 | Beneke et al. |
| 6,606,516 B2 | 8/2003 | Levine |
| 6,636,581 B2 | 10/2003 | Sorenson |
| 6,653,588 B1 | 11/2003 | Gillard-Hickman |
| 6,658,087 B2 | 12/2003 | Chalmers et al. |
| 6,663,280 B2 | 12/2003 | Doenges |
| 6,665,373 B1 | 12/2003 | Kotowski et al. |
| 6,665,433 B2 | 12/2003 | Roder |
| 6,763,635 B1 | 7/2004 | Lowman |
| 6,785,357 B2 | 8/2004 | Bernardi et al. |
| 6,812,426 B1 | 11/2004 | Kotowski et al. |
| 6,816,571 B2 | 11/2004 | Bijjani et al. |
| 6,823,039 B2 | 11/2004 | Hoheisel et al. |
| 6,837,422 B1 | 1/2005 | Meder |
| 6,839,403 B1 | 1/2005 | Kotowski et al. |
| 6,843,599 B2 | 1/2005 | Le et al. |
| 6,920,197 B2 | 7/2005 | Kang et al. |
| 7,039,159 B2 | 5/2006 | Muenchau et al. |
| 7,207,713 B2 | 4/2007 | Lowman |
| 7,418,077 B2 | 8/2008 | Gray |
| 7,471,764 B2 | 12/2008 | Kaval |
| 7,483,510 B2 | 1/2009 | Carver et al. |
| 7,486,768 B2 | 2/2009 | Allman et al. |
| 2002/0018542 A1* | 2/2002 | Fenkart et al. ............... 378/57 |
| 2004/0017887 A1 | 1/2004 | Le et al. |
| 2004/0051265 A1 | 3/2004 | Nadeau |
| 2004/0120454 A1 | 6/2004 | Ellenbogen et al. |
| 2004/0141584 A1 | 7/2004 | Bernardi et al. |
| 2004/0258194 A1 | 12/2004 | Chen et al. |
| 2005/0024199 A1 | 2/2005 | Huey et al. |
| 2005/0117700 A1 | 6/2005 | Peschmann |
| 2005/0137942 A1 | 6/2005 | LaFleur |
| 2006/0215811 A1 | 9/2006 | Modica et al. |

OTHER PUBLICATIONS

Rapiscan 520S High Performance Compact X-ray Machine, "Rapiscan", Rapiscan Security Products Ltd., p. 1, 2003.
Rapiscan X-ray Machines HM Prison Contract T601/00, "Rapiscan", Rapiscan Security Products Ltd., p. 1-2, 1999-2000.

* cited by examiner

X-RAY SECURITY INSPECTION MACHINE

CROSS-REFERENCE

The present application is a continuation of U.S. patent application Ser. No. 12/715,463, filed on Mar. 2, 2010 and issued on Jul. 3, 2012 as U.S. Pat. No. 8,213,570, which is a continuation of U.S. patent application Ser. No. 11/817,119, which issued as U.S. Pat. No. 7,702,069, which is a national stage application of PCT/GB2006/000690, having an international filing date of Feb. 27, 2006 and a priority date of Feb. 25, 2005.

FIELD

The invention relates to an X-ray security inspection machine, in particular an X-ray security inspection machine having a compact profile.

BACKGROUND

X-ray security inspection machines are widely used at security checkpoints, such as those in airports, courthouses, government offices, embassies, schools and prisons. Where space is not restricted or where an X-ray security inspection machine is required on a permanent basis, the machine may be set up and configured on site, and retained there indefinitely. Such machines are provided in various sizes and specifications, depending on their intended application. FIG. 1 shows a perspective view of such a prior art X-ray security inspection machine 1, manufactured as model 520B by Rapiscan Security Products Ltd, of West Sussex, United Kingdom (Rapiscan). The machine 1 has a standard tunnel opening 2 of 640 mm wide by 430 mm high to accommodate relatively large luggage and package sizes. The overall dimensions of the machine 1 are 2570 mm long by 1345 mm high by 835 mm wide, which is actually at the more compact end of the range for permanent machines, many of which are significantly larger.

Nevertheless, as the issue of security becomes an ever greater priority, there is an increasing demand for X-ray security inspection machines which find more widespread application. In particular, there is a need for X-ray security inspection machines which may be employed in space-restricted environments and/or which are readily movable, i.e. portable, from one location to another. X-ray security inspection machines, such as machine 1 above, suffer from a number of problems in this respect. Firstly, this type of machine is heavy, bulky and not readily portable. Secondly, the machine is too wide to be able to pass through a standard doorway, of width 765 mm, without first being disassembled. Thirdly, a skilled service technician is required to take the machine apart at its original location and to re-assemble it at its final location, which is both costly and time-consuming.

FIG. 2 shows a perspective view of another prior art X-ray security inspection machine 5, also manufactured by Rapiscan, as model 520S. The machine 5 is provided with castors 6 and a fold-up conveyor 7, which, combined with a narrow overall width of 735 mm, enables ease of movement in many situations where a full-size X-ray machine cannot be deployed. The machine 5 has overall dimensions of 2480 mm long by 1170 mm high by 735 mm wide. However, although the machine 5 is narrow and capable of passing through a standard doorway, the machine suffers from the problem of having a tunnel opening 8 of only 550 mm wide by 360 mm high. Compared with the standard tunnel opening 2 of 640 mm wide by 430 mm high, then, the machine 5 is not able to accommodate such large luggage and package sizes and is therefore of limited application.

There is a need, therefore, for an improved X-ray security inspection machine which may be employed in space-restricted environments and/or which is readily movable, i.e. portable, from one location to another. It would be desirable for such a machine to be movable without the need for a skilled service technician. It would also be desirable for such a machine to be portable without the need for disassembly. In particular, it would be desirable for such a machine to be capable of passing through a standard doorway. Furthermore, it would be desirable for such a machine to provide a tunnel opening of standard dimensions, namely of 640 mm wide by 430 mm high.

SUMMARY

The invention aims to address the above and other objectives by providing an improved X-ray security inspection machine.

According to one aspect of the invention, there is provided an X-ray security inspection machine, comprising: an X-ray tunnel for receiving an article to be inspected; a conveyor means for conveying the article through the tunnel; an X-ray source for irradiating the article within the tunnel; and an X-ray detection means for detecting X-rays transmitted through the article, wherein the X-ray detection means comprises a photodetector array module actuatable la between a first stowed configuration and a second deployed configuration.

The provision of a photodetector array module which may be moved between a stowed configuration and a deployed configuration has the advantage of reducing the width of the machine when not in use, thereby facilitating movement of the machine between locations of use, especially in space-restricted environments. What is more, because the photodetector array module may be actuated to a deployed, operational position, the dimensions of the tunnel opening of the machine are to some extent independent of the overall width of the machine when configured for relocation. For previous X-ray security inspection machines, the overall width of the machines is a function of the tunnel opening width and the width of the housing which surrounds the opening, containing control and detection electronics, power and control cables, and X-ray shielding material etc. The photodetector arrays of these machines are fixed assemblies on the general housing frameworks of the machines. Thus it has been commonly held that, in order/to provide a machine width of less than a standard doorway (765 mm), a correspondingly smaller tunnel opening is necessary. In particular, it has not been possible previously to achieve an X-ray security inspection machine having a standard tunnel opening of 640 mm by 430 mm while also having a width of less 765 mm, preferably having a width of 735 mm.

By providing a photodetector array module which may be moved independently with respect to the machine, when the module is in its stowed position, those parts of the module which contribute to its width—namely electronics, cables and shielding material—may be stored within the overall profile of the machine, occupying a region of the tunnel itself. Preferably, in this configuration, the photodetector array module is substantially flush with the X-ray machine housing. In the stowed configuration, then, the tunnel opening has a reduced size at the location of the photodetector array module. Upon actuation of the module to its deployed configuration, the module is translated away from the tunnel to project from the machine housing, thereby clearing the tunnel opening to its standard dimensions ready for use.

The X-ray security inspection machine of the invention may therefore be employed in space-restricted environments. Furthermore, the machine is readily movable, i.e., portable, from one location to another. Since the photodetector array module is stowable to provide a compact profile to the machine, which may therefore be readily moved, neither disassembly nor the services of a skilled engineer is required to move the machine. In certain embodiments, the machine has the particular advantage of being capable of providing a tunnel opening of standard dimension, namely of 640 mm wide by 430 mm high, while still being able to be passed through a standard doorway, of 765 mm width. A user of the X-ray inspection security inspection machine may therefore move the machine quickly and easily and configure the machine at its new location with minimal setting up time. The machine may therefore find ready application at smaller installations, where space is at a premium, such as in schools, prisons, offices and other areas where it is difficult to install a conventional X-ray facility.

Preferably, the photodetector array module is actuatable by a linear actuation means coupled to the module. Preferably, the actuation means employs a linear guide rail to define the direction of motion of the photodetector array module, so that its movement between stowed and deployed configurations is consistently reproducible.

Preferably, the photodetector array module comprises two substantially perpendicular photodetector arrays, in an "L"-shaped arrangement, one of the arrays being disposed across a top region of the tunnel and the other array being disposed across a side region of the tunnel. Preferably, the X-ray detection area provided by the first photodetector array is supplemented by a further photodetector array, which is provided adjacent the first array, on the opposite side from the second array, and is positioned in fixed relation to the X-ray machine. The stationary photodetector array is preferably positioned at a vertically higher level than the first photodetector array, so that when the photodetector array, module is retracted to its stowed configuration, a part of the first photodetector array slides under the stationary photodetector array, the two arrays then at least partially overlapping. This has the advantage of providing a relatively large and uninterrupted/continuous X-ray detection area at the upper region of the tunnel, in the deployed configuration, but because of the two-part, overlapping arrangement of the stationary and first photodetector arrays in the stowed configuration, the width of the photodetector array module itself is smaller than the overall X-ray detection width of the X-ray detection means, providing the advantages discussed above.

Preferably, the substantially uninterrupted X-ray detection area equals the overall X-ray detection area provided by the X-ray detection means in the first substantially planar extent.

Preferably, the photodetector array module is translated between approximately 60 mm to 100 mm, but particularly 80 mm, between the stowed configuration and the deployed configuration of the module.

Preferably, a control console for controlling operation of the X-ray security inspection machine is also stowable into the machines housing. Preferably still, deployment of the control console is performed automatically with actuation of the photodetector array module. In this way, activation of the machine quickly deploys the machine to its configuration ready for use.

According to a further aspect of the invention, there is provided a conveyor belt-tracking device for tracking a conveyor belt of an X-ray security inspection machine in a straight line, the device comprising a guide frame arranged to receive the conveyor belt and substantially to restrict motion of the conveyor belt to a predetermined direction.

A problem with conveyor belt systems is that the conveyor belt tends to track off center, which can result in damage to the machine in two ways. Firstly, the conveyor belt itself can become worn and need replacing. Secondly, the belt can cut through cables inside the machine, which is both dangerous and may prevent operation of the machine altogether. The provision of a guide frame which receives the conveyor belt and constrains its motion to a predetermined direction provides the advantage of keeping the belt tracked in a straight line, so that it may not move away from this line.

Preferably, the guide frame has upper and lower runner portions between which the conveyor belt slides, so that movement of the conveyor belt in all directions perpendicular to the predetermined direction may be substantially prevented.

According to a further aspect of the present invention, there is provided an X-ray security inspection machine, comprising: an X-ray tunnel for receiving an article to be inspected; a conveyor means for conveying the article through the tunnel; an X-ray source for irradiating the article within the tunnel; and an X-ray detection means for detecting X-rays transmitted through the article, the X-ray detection means comprising: a first unit having a first photodetector array; and a second unit having a second photodetector array and being offset with respect to the first unit, wherein the first and second units are movable relative to one another between a first arrangement in which the first and second photodetector arrays overlap to a first degree and a second arrangement in which the first and second photodetector arrays overlap to a second, lower degree.

The provision of a two-part X-ray detection means, with the two units being offset with respect to and movable relative to one another, allows the X-ray detection area of the X-ray detection means to be varied, according to the degree of overlap of the units. A maximum continuous X-ray detection area is provided when the two photodetector arrays have zero degree of overlap, but are adjacent one another (so that projections of their individual X-ray detection areas onto the same projection plane would adjoin one another). A greater degree of overlap will reduce the continuous X-ray detection area. When the two photodetector arrays fully overlap, i.e. when one unit is fully obscured by the other unit, only the unobscured unit is used for X-ray detection.

Of course, when the two units overlap, the width of the X-ray detection means is reduced. In this way, the same advantages discussed above are achievable, since the units may be arranged to overlap when the machine is not in use—thereby providing a more compact machine profile for maneuverability in confined areas—and to move apart from each other to reduce the degree of overlap when set up for use—thereby providing an X-ray detection area and corresponding tunnel size of greater size, particularly of the standard dimensions specified above.

Other preferred features and advantages of the invention are set out in the description and in the dependent claims which are appended hereto.

BRIEF DESCRIPTION OF THE DRAWINGS

The invention may be put into practice in a number of ways and some embodiments will now be described, by way of non-limiting example only, with reference to the following figures, in which.

DETAILED DESCRIPTION

Figure 1:
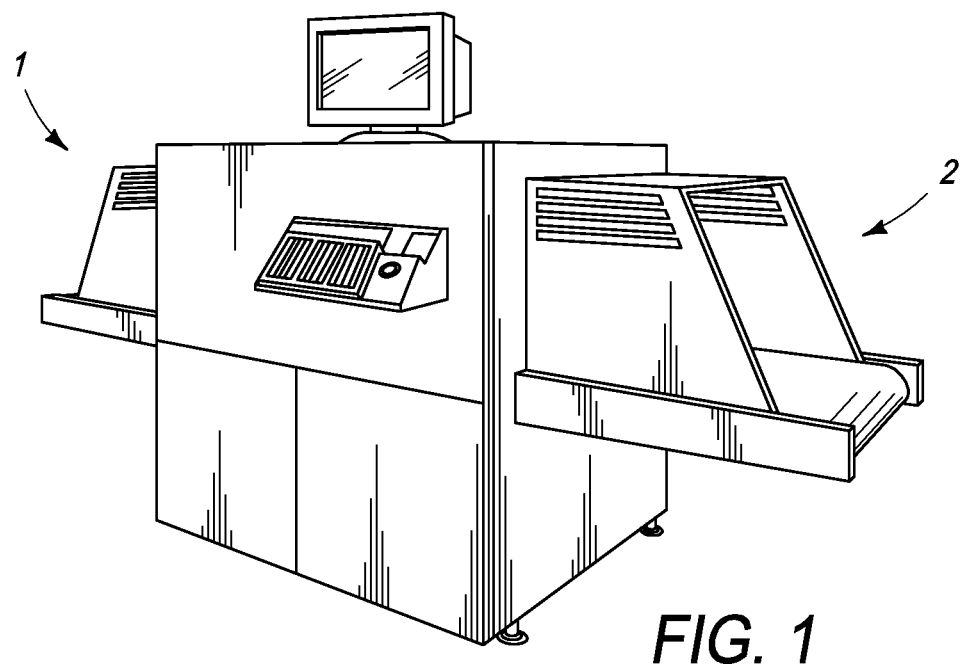
FIG. 1 shows a perspective view of a prior art X-ray security inspection machine, intended for substantially permanent installation.
Figure 2:
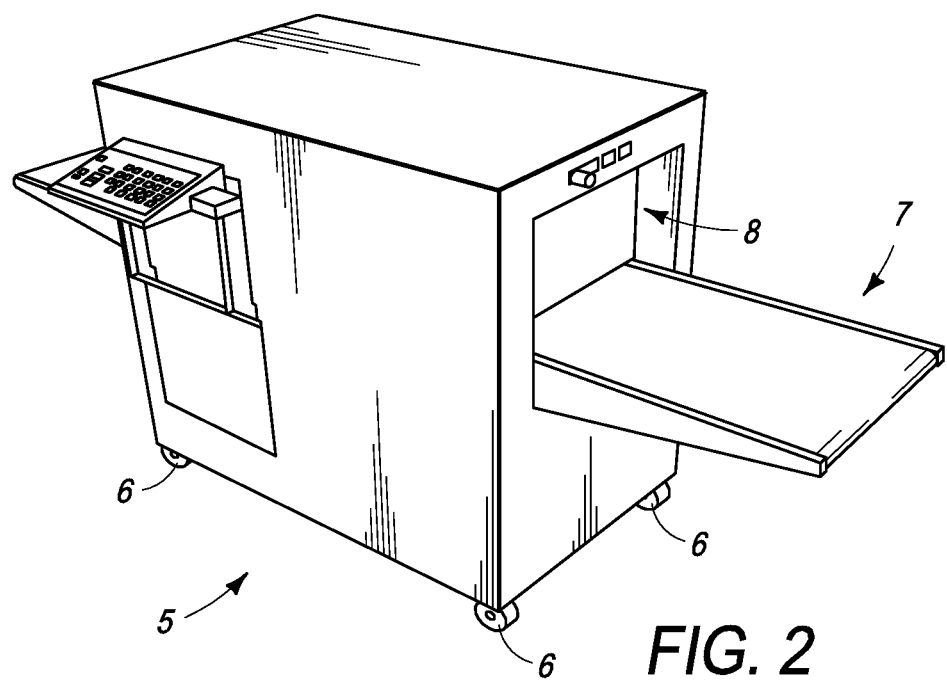
FIG. 2 shows a perspective view of a prior art portable X-ray security inspection machine.
Figure 3:
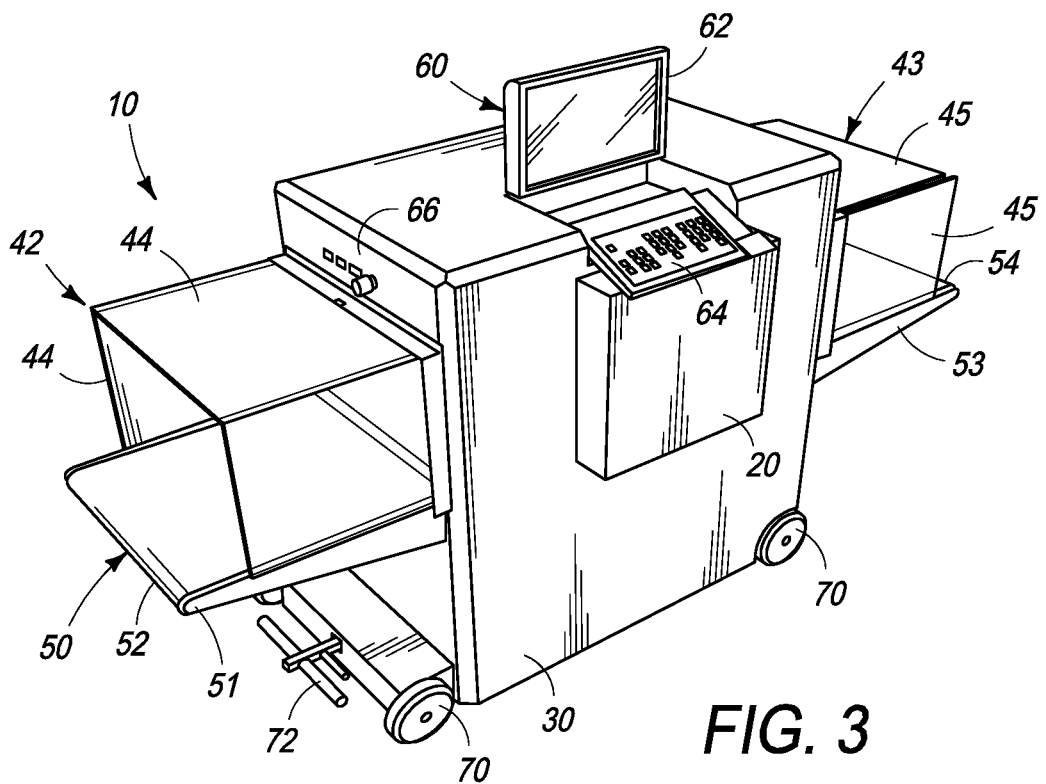
FIG. 3 shows a perspective view of an X-ray security inspection machine according to a first embodiment of the invention, in which the machine is deployed for use.

Referring to FIG. 3, there is shown an X-ray security inspection machine 10 in accordance with a first embodiment of the invention. In this embodiment, the machine is fully deployed ready for use. A photodetector array module 20 has been extended to its deployed position and projects from the X-ray machine's housing 30. The extent of projection of the photodetector array module 20 is typically between 60 mm and 100 mm, but/preferably the module extends by approximately 80 mm from the housing.

Contained within the housing 30 are the necessary components for providing an X-ray security inspection machine, including an X-ray generator, processing and control electronics, power and control cables, a computer processor and memory storing suitable operational software, and X-ray shielding material, as will be understood by the skilled person.

Above the X-ray generator (not shown) within the housing 30 and below the upper surface of the photodetector array module 20, the housing defines a tunnel 40, having a substantially rectangular tunnel opening 41. Items to undergo X-ray inspection in the machine 10 pass through the tunnel 40 for irradiation by X-ray photons. Those photons which are transmitted through the item under inspection are then detected. The tunnel opening 41 has standard dimensions of 640 mm wide by 430 mm high, in this embodiment.

The tunnel 40 passes through the housing 30 from an input side 42 to an output side 43. In order to help define a maximum item size which may be inspected with the machine 10, a respective plurality of tunnel wall panels 44, 45 are disposed around the tunnel openings at the input and output sides 42, 43. The panels are preferably made of a transparent plastics material, such as polycarbonate, plexiglas™ or perspex™, to facilitate observation of items passing into and out of the tunnel 40.

A conveyor system 50 transports items for inspection from the input side 42 of the tunnel 40 to its output side 43. In the embodiment shown in FIG. 3, the conveyor system 50 comprises three separate conveyors: an input conveyor 51 having an associated conveyor belt 52; an output conveyor 53 having an associated conveyor belt 54; and an intermediate conveyor (not shown) located within the tunnel 40 and having its own associated conveyor belt (also not shown). Other arrangements of the conveyor system will be readily apparent to the skilled person.

The X-ray security inspection machine 10 incorporates a control console 60, comprising a monitor 62 and a keypad/mouse pad 64, by means of which an operator may control the machine. The control console 60 is stowable, so that it does not contribute to the overall width of the machine 10, when in its stowed configuration.

Initial activation and subsequent deactivation of the machine 10 are achieved by means of activation control switches 66, which are accommodated on the housing 30, preferably not on either lateral sides of the machine, so as not to increase the width profile of the machine. The activation controls 66 may include a key switch to ensure operation only by authorised personnel, or the like.

The X-ray security inspection machine 10 is provided with a set of wheels or castors 70, on which the machine is supported and by means of which the machine may be moved. The wheels 70 may be standard nylon wheels, conventionally used. However, nylon wheels tend to be relatively hard which makes movement of the machine over certain surfaces, especially uneven surfaces, somewhat difficult. Preferably, the wheels are provided by rubber castors, which are capable of conforming more readily to surface unevenness and reducing the impact on the machine when encountering such surfaces. This specification of wheel also reduces vibration of the machine during transportation. In order to facilitate such movement, a steering and braking handle 72 is provided. The steering and braking handle 72 co-operates with the wheels 70, at least to provide a braking mechanism if not also to provide a steering mechanism for changing direction of the machine. In the deployed configuration of the machine 10 ready for use, the steering and braking handle 72 is itself stowed away beneath the machine, as shown in FIG. 3.

Figure 4:
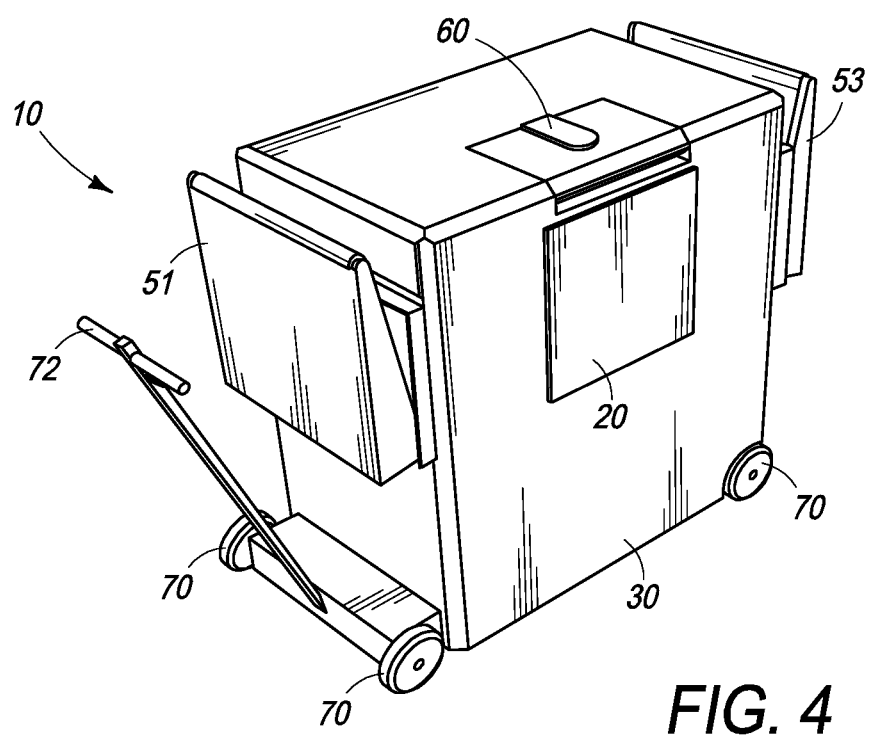
FIG. 4 shows a perspective view of the embodiment of FIG. 3, in which the machine is in its stowed configuration ready to be moved.

FIG. 4 shows the embodiment of FIG. 3 when the machine 10 is in its stowed configuration, ready to be moved from one location to another. The photodetector array module 20 has been retracted towards the tunnel 40, so that its outer surface is substantially flush with the machine housing 30. The control console 60 has also been stowed away, the keypad/mouse pad 64 having been dropped down and translated towards the center of the machine, and the monitor 62 having been folded down over the keypad/mouse pad to lie substantially flush with the surrounding housing 30. In particular, retraction of the keypad/mouse pad 64 into the housing 30 means that the width of the machine 10 is substantially that of the housing itself and is not increased by the photodetector array module 20 or control console 60.

The tunnel wall panels 44, 45 are foldable panels, such that the generally vertical panels (in the deployed configuration) fold onto the generally horizontal panel, which itself folds down towards the tunnel opening 41 at its respective input or output side 42, 43. The input and output conveyors 51, 53 are also hingedly attached to the machine housing 30, such that they may be folded upwards to cover the tunnel opening 41, in their stowed positions.

Finally, the steering and braking handle 72 has been drawn out from its stowed position under the machine 10, to assist the movement of the machine. The handle 72 cooperates with a braking mechanism via a lever, which in FIG. 4 has been released, to permit free rotation of the wheels 70. The steering handle 72 may be a simple couple to the machine 10 for pushing or pulling the machine from one location to another. Alternatively, the handle 72 may be coupled to a pivoting wheel assembly (not shown), to facilitate changes of direction when the machine is moved.

Once the machine 10 is wheeled to a desired location, the brake associated with the steering and braking handle 72 is applied and the handle is stowed away into the housing 30 at the bottom of the machine. Next, the input and output conveyors 51, 53 are folded down to a substantially horizontal orientation. The tunnel wall panels 44, 45 are folded out around the tunnel opening 41 on either side. The monitor 62, which is preferably a LCD monitor, is provided with a quick-release latching mechanism, so that once pressed down, the control console 60 opens out. The monitor 62 opens up automatically and the keypad/mouse pad 64 protrudes forward and is inclined, for use. The activation control 66 is next operated, to turn the machine 10 on. Upon activation, the photodetector array module 20 is translated from its stowed configuration to its deployed configuration, protruding from the housing 30 in its final operational position. During this sequence, the machine's control systems perform radiation checks and other standard software checks, to ensure that the machine is operational. Following this procedure, the machine is ready for use.

Figure 5:
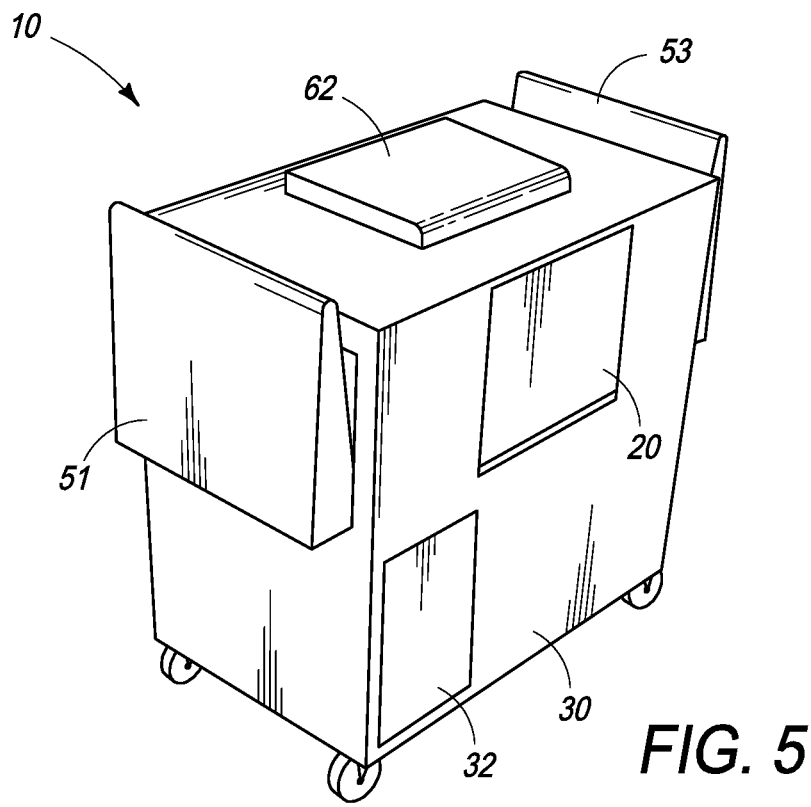
FIG. 5 shows a perspective view of an X-ray security inspection machine according to a second embodiment of the invention, in which the machine is in its stowed configuration.
Figure 6:
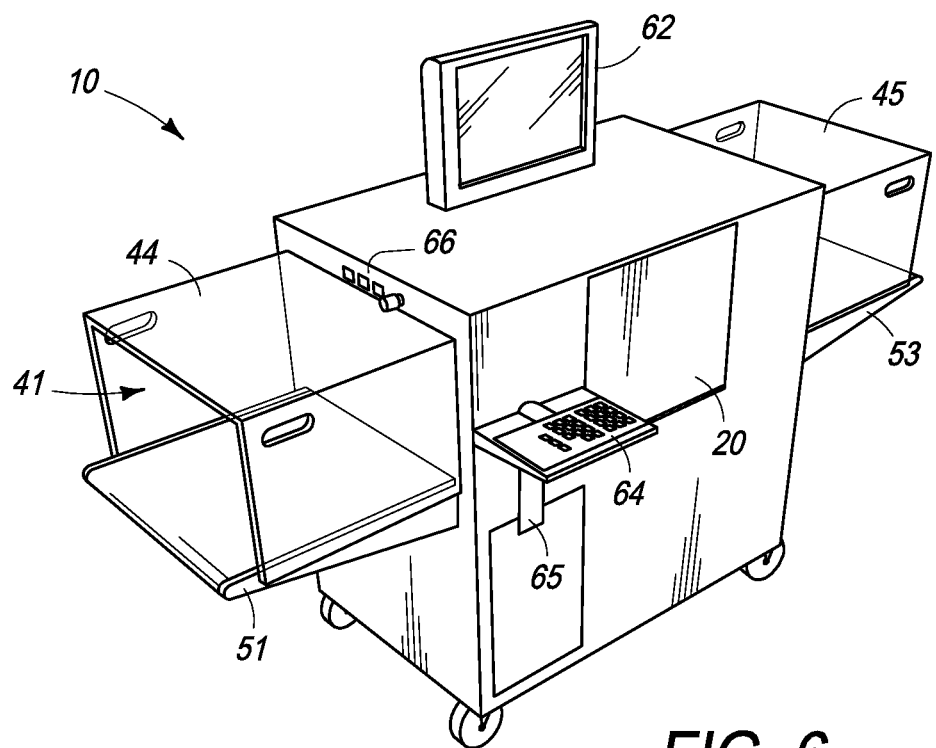
FIG. 6 shows a perspective view of the embodiment of FIG. 5, at an intermediate stage of deployment for use.
Figure 7:
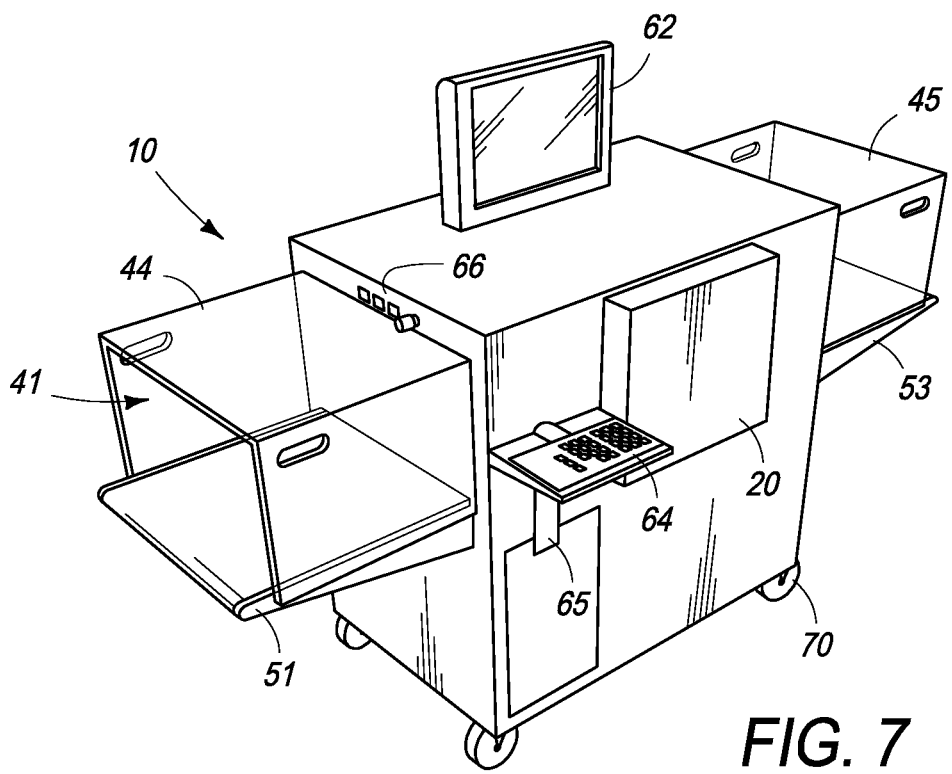
FIG. 7 shows a perspective view of the embodiment of FIG. 5, in which the machine is deployed for use.

FIGS. 5 to 7 illustrate the above sequence with reference to a second embodiment of the invention. In FIG. 5, the machine 10 is in its stowed configuration suitable for transportation of the machine. In this embodiment, the control console 60 is provided as a different arrangement from the previous embodiment, and the screen 62 and keypad/mouse pad 64 are not arranged to deploy automatically, nor in concert. The monitor 62 is positioned on top of the housing 30 and is arranged to pivot between a stowed position, substantially parallel with the top surface of the housing and an operational position, substantially normal to the upper surface of the housing. The keypad/mouse pad 64 is stowed in a storage compartment 32 spaced away from the photodetector array module 20. As in the previous embodiment, the photodetector array module 20 is substantially flush with the side surface of the housing 30 when in the stowed configuration.

FIG. 6 shows the machine 10 at the stage where manual deployment of various parts of the machine has been completed. In particular, the input and output conveyors 51, 53 and their associated tunnel wall panels 44, 45 have been folded out to their operational configuration. The monitor 62 has been pivoted upwards from its stowed position and the keypad/mouse pad 64 has been drawn out from its storage compartment 32 and is supported by a stand 65.

Up until this point, the machine 10 has not actually been switched on. Operation of the activation controls 66 is required to initialize the machine and to deploy the photodetector array module 20. Upon such operation, the photodetector array module 20 slides out from the housing 30 to its operational configuration, as shown in FIG. 7. Following deployment of the module 20, the tunnel opening 41 is uniform along its length, at the standard dimensions of 640 mm by 430 mm, in this embodiment. The machine width in its stowed configuration (i.e., that of the housing 30) is approximately 750 mm, and the machine width in its deployed configuration (i.e., taking account of the extension of the photodetector array module 20 and the keypad/mouse pad 64) is approximately 855 mm.

Figure 8:
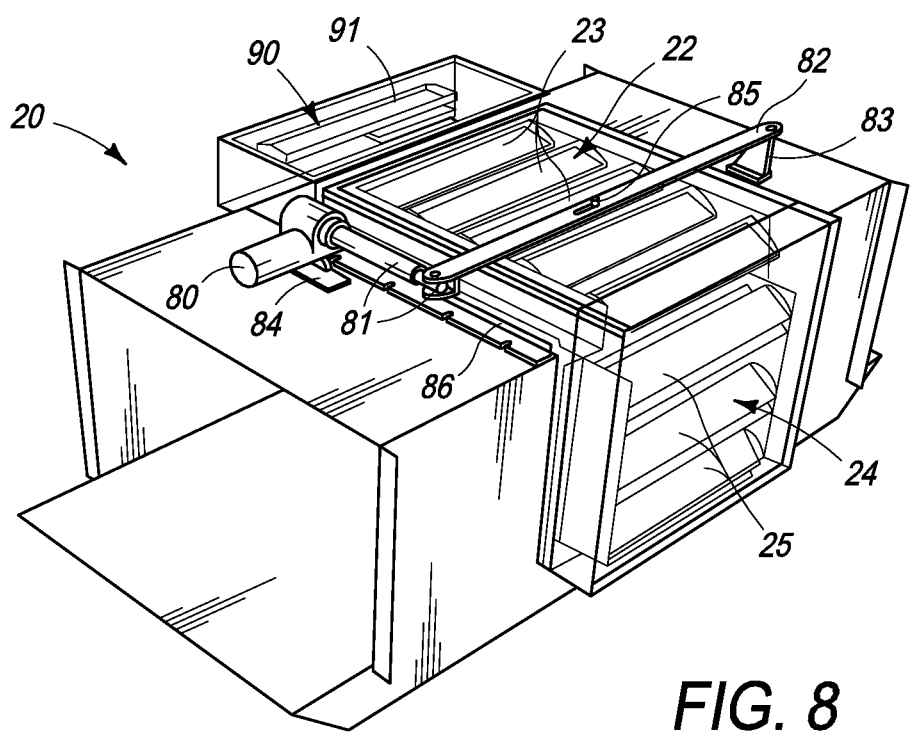
FIG. 8 shows a perspective view of a photodetector array unit according to an embodiment of the invention.

FIG. 8 shows a perspective view of the photodetector array module 20, without its casing and without the surrounding housing 30 of the machine 10. In this embodiment, the photodetector array module 20 comprises a first photodetector array 22, which extends substantially in a first plane, and a second photodetector array 24, which extends substantially in a second plane perpendicular to the first plane. Thus first and second photodetector arrays 22, 24 form an "L"-shaped photodetector array. In the embodiment shown in FIG. 8, the first and second photodetector arrays 22, 24 are provided by respective photodetector array boards 23, 25 fixed to corresponding board supports arranged generally along the first and second planes.

In the preferred embodiment of the invention, the X-ray generator of machine 10 is oriented vertically upwards and produces a fan-shape X-ray beam, which scans items under inspection on the conveyor system 50, to produce an image of the contents of the item on monitor 62. Successive sections of the item under inspection are exposed to the narrow linear X-ray beam as the conveyor system moves the item relative to the beam. X-ray photons which are transmitted through the item and reach the photodetector arrays are then detected. The transmitted light pattern so detected is characteristic of the item being scanned. As the transmitted light is received by the array of photodetectors, the photodetectors generate electrical signals in accordance with the intensity of that received light. This may be achieved either directly, using photodiodes sensitive to X-rays, or indirectly, by using an X-ray phosphor, or scintillator, arranged over photodiodes sensitive to light of the wavelength(s) generated by the scintillator. In either case, the outputs of the photodetectors are sampled in sequence to provide a series of signals in accordance with the light received by the photodetectors. These signals are converted to digital form and stored in a memory and may also be transmitted to the monitor 62 via suitable video output circuits, so that an image representative of the item under inspection may be viewed.

As discussed above, the photodetector array module 20 is translatable between a stowed position, in which the second photodetector array 24 is substantially contained within the tunnel opening 41, and a deployed position, in which the tunnel opening is unobstructed and the second photodetector array projects beyond the outer side surface of the machine housing 30. In the embodiment of FIG. 8, the photodetector array module 20 is actuatable by means of a linear actuator 80, having an extendible and retractable arm 81. The actuator arm 81 is pivotally attached at one end to a freely pivoting arm 82. The other end of the pivoting arm 82 is pivotally attached to a bracket 83, itself fixed with respect to the machine 10 via an upper surface of the tunnel 40. The linear actuator 80 is also held in fixed relation to the machine 10 via corresponding bracket 84, which is fixed to an upper surface of the tunnel 40, on the other side of the photodetector array module 20 than bracket 83.

Thus, actuation of linear actuator 80 to extend or retract the actuator arm 81 causes the pivoting arm 82 to pivot about its joint with bracket 83. The linear, translational component of the rotational motion of the pivoting arm 82 is transmitted to the photodetector array module 20 by means of a sliding couple 85 provided at the center of the pivoting arm 82, which extends across the first photodetector array 22. In this embodiment, the sliding couple 85 is provided by a longitudinally extending slot formed in the pivoting arm 82 and a co-operating pin formed on the upper surface of the photodetector array module 20 and extending through the slot. Rotational motion of the pivoting arm 82 is thereby transformed into linear, translational motion of the photodetector array module 20, so that the module may be translated into and out of the stowed position.

In order to ensure precision motion of the photodetector array module 20, a guide rail and roller assembly 86 is provided. The guide rail is fixed to an upper surface of the tunnel 40 and the rollers are provided on the photodetector array module 20, co-operatively engaging with the guide rail so as to ensure smooth linear motion of the module 20.

By appropriate selection of the pivot point between pivoting arm 82 and bracket 83, and of sliding couple 85, translation displacement of the photodetector array module 20 may be set within a predetermined distance range. Such a range corresponds to a minimum and maximum extension of the actuator arm 81, from being extended from its fully retracted position to its fully extended position by linear actuator 80. In the present embodiment, the desired translational displacement of the photodetector array module 20 is approximately 80 mm. Being able to reproduce consistently this extension of the module 20 results in a corresponding reproducibility in the alignment of the photodetector arrays.

Fixed in relation to the tunnel 40 and the machine 10 generally, is a stationary, third photodetector array 90, provided on a third photodetector board 91 and associated board support. The stationary photodetector array 90 is positioned adjacent the first photodetector array, at an opposite end to that of the second photodetector array 24, so that, upon actuation of the photodetector array module 20, the first photodetector array 22 moves towards or away from the stationary photodetector array 90.

The third photodetector array board 91 is positioned at a vertically different level from the first photodetector array board 23 closest to the third photodetector array. As such, when the first detector array 22 is translated towards the third photodetector array 90, the two arrays do not come into physical contact with each other. Instead, the first part of the first photodetector array 22 (i.e. the first photodetector array board 23) slides under the third photodetector array board 91, so that the two at least partially overlap one another. In the deployed configuration, the photodetector array boards 23, 91 may partially overlap to a lesser degree than in the stowed configuration, or may not overlap at all.

In this way, in the deployed configuration, an X-ray detection area lying generally in the first plane is provided by a combination of the first photodetector array 22 and the stationary photodetector array 90; that is, the X-ray detection area provided by the first photodetector array 22 is smaller than the overall X-ray detection area provided by the machine 10 in the generally first plane, since the stationary, third photodetector array 90 supplements the first photodetector array. The movable first and second photodetector arrays 22, 24 and the stationary, third photodetector array 90 can be considered to form together a two-part photodetector array "box".

Although the X-ray detection area generally in the first plane may be provided with a predetermined width to accommodate a desired tunnel opening width, because of the separate, first and third photodetector arrays which may move relative to one another and more importantly overlap, the overall width of the machine 10 when not in use is advantageously reduced from that which has been conventionally achievable with prior art machines.

Figure 9:
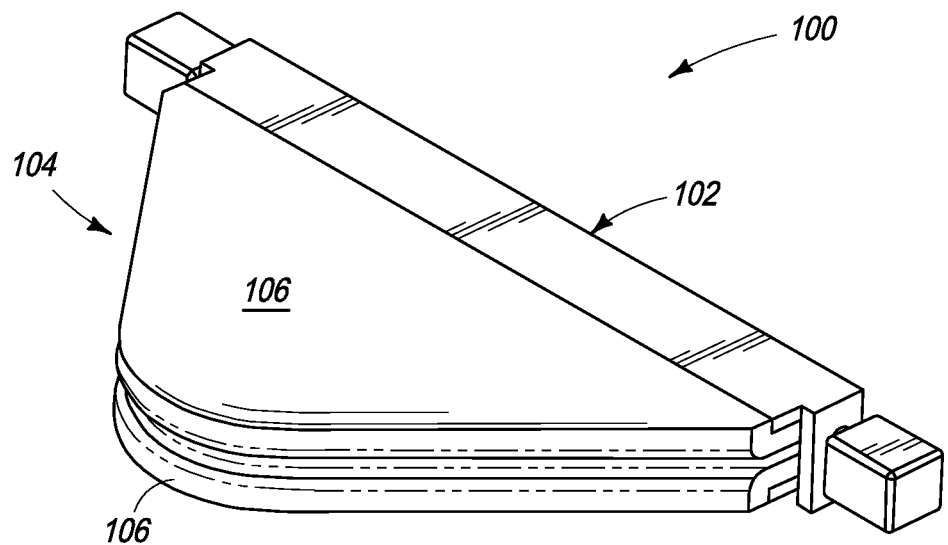
FIG. 9 shows a perspective view of a belt-tracking device in accordance with an embodiment of the invention.
Figure 10:
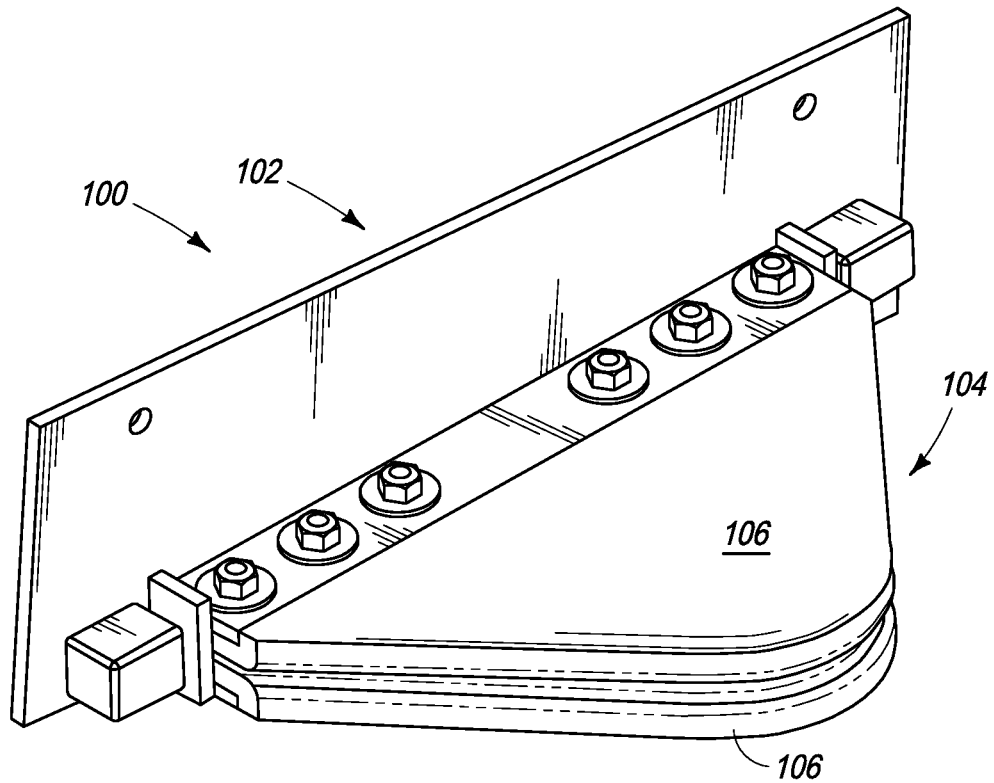
FIG. 10 shows a perspective view of the belt-tracking device in accordance with a further embodiment of the invention.

FIGS. 9 and 10 show perspective views of a conveyor belt-tracking device 100, which may be used to maintain the tracking of a conveyor belt in an X-ray security inspection machine, to prevent the belt from tracking off line and cutting cables and/or damaging the belt. The tracking device 100 includes a mounting bracket 102, for mounting the device to a conveyor system 50 and a guide frame 104 arranged to receive the conveyor belt and substantially to restrict the motion of the conveyor belt to a predetermined direction, defined by the guide frame. In the embodiments shown in FIGS. 9 and 10, the guide frame comprises an upper and a lower runner portion 106, which overlie another and extend from the mounting bracket 102 to form generally rounded triangular projections from the mounting bracket 102. The upper and lower runner portions 106 are spaced apart from one another, so that a conveyor belt may run between the two portions and not only prevent lateral movement of the conveyor belt away from the predetermined direction but also to prevent unwanted movement of the conveyor belt in substantially all directions perpendicular to the predetermined direction.

Figure 11:
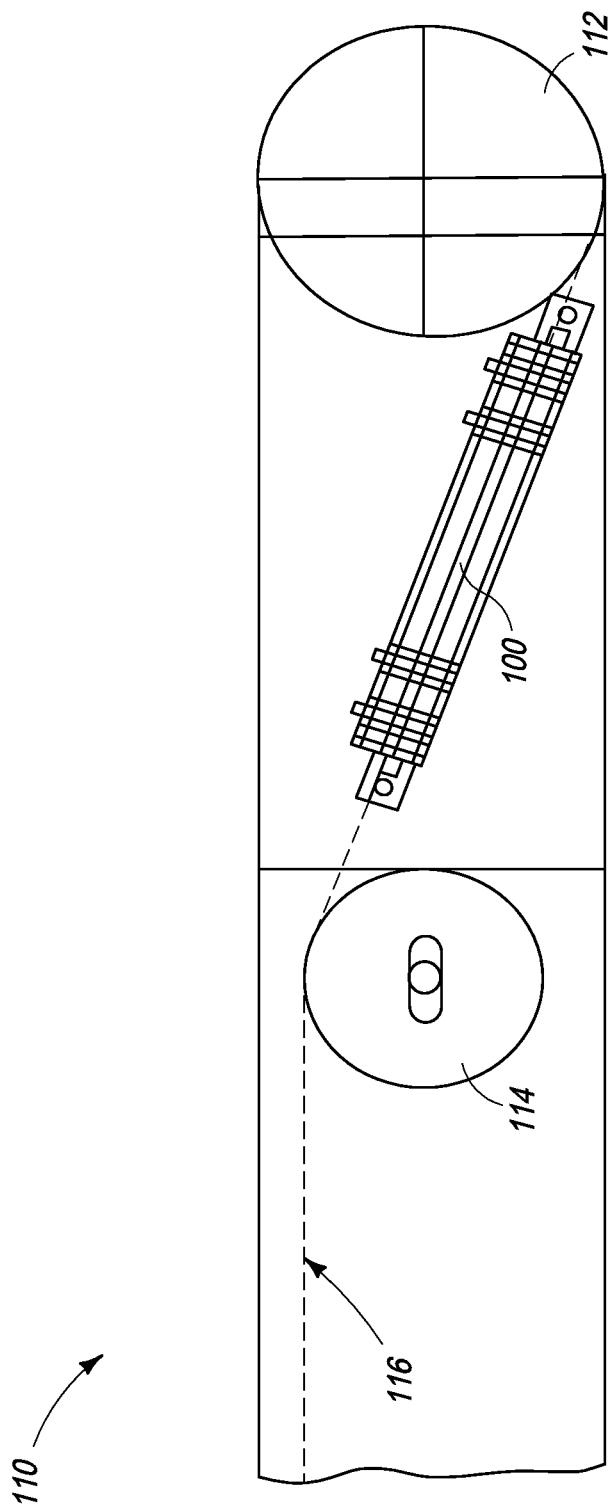
FIG. 11 shows a side sectional view of a conveyor and the belt-tracking device in accordance with a still further embodiment of the invention.

FIG. 11 shows a side sectional view of a conveyor 110, having an idle roller 112 and a tracking roller 114, about which passes a conveyor belt 116. The belt-tracking device 100 of the invention is mounted in this embodiment between the idle and tracking rollers 112, 114, to receive the conveyor belt 116 and to maintain its tracking. In another embodiment, two belt-tracking devices 100 may be positioned opposite one another on either side of the conveyor belt 116. In other embodiments, the belt-tracking device 100 may be located at any suitable position along the conveyor system, where tracking of the belt is desirable or needed.

Preferably, the edges of the runner portions 106 are rounded off so as to reduce wear on the conveyor belt as a result of its interaction with the belt-tracking device 100. The conveyor belt-tracking device 100 of the invention resolves the problem of the conveyor belt tracking off line and causing damage to an X-ray security inspection machine and thereby reduces maintenance costs for such a machine.

The invention has been described with reference to the above specific embodiments. However, the skilled person would readily appreciate that features of one embodiment may be equally incorporated into the other embodiments. In addition, the skilled person will readily envisage alternatives, equivalents and modifications to the specific embodiments described above, which may be used to put the invention into practice. For example, the linear actuator 80 could be coupled to the photodetector array module 20 without the use of the pivoting arm 82. In addition, two such linear actuators could be positioned on either side of the photodetector array module 20 to provide the linear motion. In fact, any actuator capable of providing the desired translation of the photodetector array module 20 could be used.

As to the control console 60, this may be deployed and retracted purely manually, or by means of a quick release latching mechanism which, once operated, causes a substantially automatic deployment of the console. Alternatively, the control console 60 may be deployed electromechanically. Such deployment may be by means of a mechanism coupled to the photodetector array module actuator so that both the photodetector array module and the control console are deployed together, automatically.

The invention claimed is:

1. An X-ray security inspection machine, comprising:
   a machine housing defining an X-ray tunnel for receiving an article to be inspected;
   a first conveyor belt for conveying the article;
   a first roller for receiving and moving the conveyor belt;
   a second roller for receiving and moving the conveyor belt, wherein the first roller is spaced from the second roller by a distance and wherein the distance defines a path for the conveyor belt; and
   a conveyor belt tracking device positioned along said path, wherein the conveyor belt tracking device comprises:
      a mounting bracket for mounting the conveyor belt tracking device to the inspection machine;

a guide frame comprises an upper portion and a lower portion, wherein said upper portion and lower portion are spaced apart from each other, wherein one end of the upper portion and lower portion are connected to the mounting bracket and the other end of the upper portion and lower portion extend outward from the mounting bracket to form generally rounded and triangular projections, and wherein the conveyor belt passes through the space between the upper portion and lower portion.

2. The X-ray security inspection machine of claim 1 wherein the upper and lower portions overlie each other to form the generally rounded and triangular projections.

3. The X-ray security inspection machine of claim 1 further comprising a second conveyor belt tracking device placed along said path.

4. The X-ray security inspection machine of claim 1 further comprising a second conveyor belt and a third conveyor belt.

5. The X-ray security inspection machine of claim 4 wherein the first conveyor belt is an intermediate conveyor belt located within the tunnel, the second conveyor belt is an input conveyor belt, and the third conveyor belt is an output conveyor belt.

6. The X-ray security inspection machine of claim 4 wherein the first conveyor belt is an input conveyor belt, the second conveyor belt is an intermediate conveyor belt located within the tunnel, and the third conveyor belt is an output conveyor belt.

7. The X-ray security inspection machine of claim 4 wherein the first conveyor belt is an output conveyor belt, the second conveyor belt is an intermediate conveyor belt located within the tunnel, and the third conveyor belt is an input conveyor belt.

\* \* \* \* \*